United States Patent [19]

Reeves

[11] Patent Number: 4,534,210
[45] Date of Patent: Aug. 13, 1985

[54] APPARATUS AND METHOD FOR MEASURING THE VISCOSITY OF A LIQUID

[76] Inventor: Timothy J. Reeves, 5 Rosdin Lodge, Prince's Ave., Windsor, Randburg, Transvaal, South Africa

[21] Appl. No.: 540,813

[22] Filed: Oct. 11, 1983

[30] Foreign Application Priority Data

Oct. 11, 1982 [ZA] South Africa .................. 82/7413

[51] Int. Cl.³ ............................................ G01N 11/14
[52] U.S. Cl. ............................................................ 73/59
[58] Field of Search ........................................ 73/59, 54

[56] References Cited

U.S. PATENT DOCUMENTS

| | | | |
|---|---|---|---|
| 2,171,312 | 8/1939 | Meyers | 73/59 X |
| 3,057,187 | 10/1962 | Read et al. | 73/59 X |
| 3,488,995 | 1/1970 | Zimmerman | 73/59 |
| 3,777,551 | 12/1973 | Weiss | 73/59 |
| 4,151,744 | 5/1979 | Hemmings | 73/54 |

FOREIGN PATENT DOCUMENTS 55-75635  6/1980  Japan .................................. 73/59

Primary Examiner—Stewart J. Levy
Assistant Examiner—Joseph W. Roskos
Attorney, Agent, or Firm—Ladas & Parry

[57] ABSTRACT

In the method, part of the liquid flow in a circuit is continuously withdrawn. A substantially constant head is established in the liquid drawn off, and at least some of this liquid is allowed to flow under gravity at a constant rate past a rotor rotated by a motor, so causing drag on the rotor in accordance with its viscosity. An operationing characteristic of the motor, such as its speed or the current which it draws, is monitored to provide an indication of the viscosity of the liquid. The constant head is established in one limb of a U-shaped chamber by means of a weir set at a predetermined height above the rotor, which is arranged in a downwardly directed passage surrounded annularly by the other limb of the chamber.

15 Claims, 1 Drawing Figure

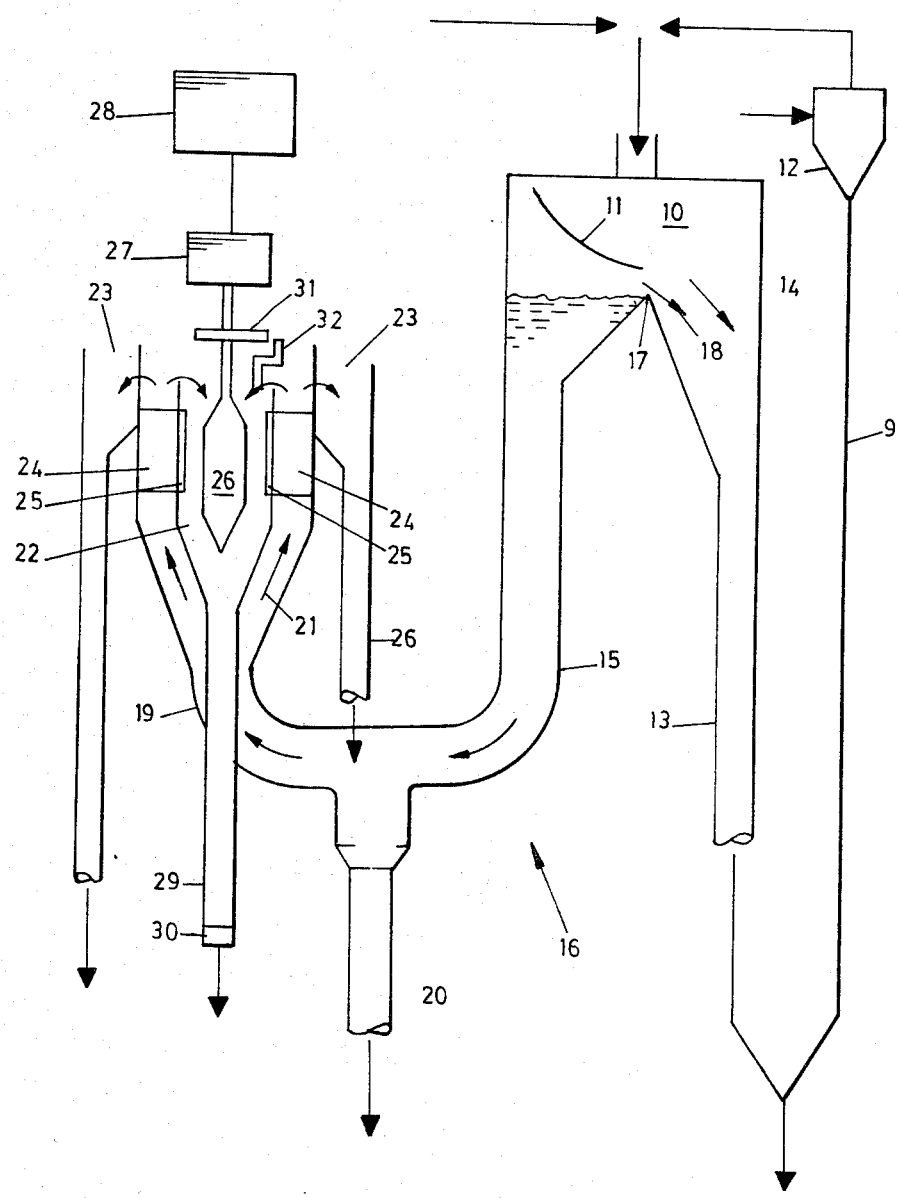

APPARATUS AND METHOD FOR MEASURING THE VISCOSITY OF A LIQUID

BACKGROUND TO THE INVENTION

This invention relates to an apparatus and method for use in measuring the viscosity of a liquid. In one application, the apparatus and method can be used to measure the viscosity of a dense medium such as a suspension of ferrosilicon in the art of diamond recovery, the term "liquid" being intended to include suspensions.

Up to now, viscosity measurements have usually been made in a laboratory under controlled conditions. This involves the extraction of a sample of the liquid to be tested, and the introduction of the sample to an independent apparatus. One such apparatus is described in the specification of U.K. patent application No. 174377/77. Here, the sample is pumped upwardly in one limb of a U-shaped chamber past a bobbin arranged to rotate in the liquid. The motor driving the bobbin is either set to rotate the bobbin at constant angular velocity, or to draw constant current. In the former case, the current drawn is monitored, and used to give an indication of viscosity in terms of a known relationship between current drawn and drag on the bobbin, which in turn is dependent on viscosity. In the latter case, the motor speed, which is dependent on the drag on the rotating bobbin and hence on the viscosity of the liquid, is monitored to give an indication of viscosity.

The main disadvantage of an apparatus of this nature is that it is necessary to take periodic samples from the medium as it flows around its circuit. Continuous monitoring is not possible. A further disadvantage is that, if the apparatus should fail to operate, the liquid sample under test will merely remain in the apparatus. In a case where the liquid is a dense medium such as a suspension of ferrosilicon, this can result in clogging of the apparatus and wastage of time in clearing it for re-use.

SUMMARY OF THE INVENTION

The invention provides an apparatus for the continuous measurement of the viscosity of a liquid flowing in a circuit, the apparatus including means for continuously drawing off part of the flow of the liquid in the circuit, means for establishing a substantially constant static head in the liquid drawn off, means for allowing at least some of this liquid to flow at a constant flow rate under gravity past a rotor arranged to be rotated by a motor so that the liquid exerts a drag on the rotor in accordance with its viscosity and means for measuring an operating characteristic of the motor to give an indication of the viscosity of the liquid.

Preferably, the means for establishing a constant static head in the liquid drawn off includes a static head chamber provided with an overflow weir at a predetermined height above the rotor. Preferably, the weir is situated at the head of a downwardly extending limb of a U-shaped chamber, the other limb of which extends upwardly to a level lower than that of the weir, so that liquid flowing under gravity through the chamber can overflow at the top of the other limb. The height of the weir with respect to the rotor may be adjustable. The upper end of the upwardly extending limb may be arranged so that liquid flowing through the chamber overflows partially into a downwardly extending passage containing the rotor and partially to waste, with the overflow to waste being situated slightly higher than the overflow to the passage.

There may be a drain situated in the portion of the chamber linking the limbs to allow part of the liquid flowing through the chamber to flow to waste, and to allow liquid to escape from the chamber when the apparatus is not in use.

In a preferred embodiment of the invention, the motor is arranged to rotate the rotor at constant angular speed, and the measuring means are arranged to make a continuous measurement of the current drawn by the motor. Preferably, the motor is a D.C. motor and means are provided for keeping the motor temperature constant during operation. In another embodiment, however, it is possible for the motor to be supplied with a constant current and for the motor speed to be measured continuously by the measuring means. Means may be provided for automatically flushing out the passage containing the rotor with water in the event that the apparatus ceases to function.

The invention also provides a method for continuously measuring the viscosity of a liquid flowing in a circuit, the method including the steps of continuously drawing off a part of the liquid flow in the circuit, establishing a substantially constant static head in the liquid drawn off, allowing the liquid to flow at a constant rate under gravity past a rotor so that the liquid exerts a drag on the rotor in accordance with its viscosity, rotating the rotor by a motor and measuring an operating characteristic of the motor to give an indication of the viscosity of the liquid.

BRIEF DESCRIPTION OF THE DRAWING

The drawing shows a diagrammatic illustration of an apparatus of the invention, which is intended for use in testing liquid suspensions.

DESCRIPTION OF A PREFERRED EMBODIMENT

In the drawing, the flow direction of liquid to be tested is depicted by arrows. Liquid is tapped from the operating circuit (not shown) and is fed to a chamber 10 containing a sieve bend 11. The liquid can be fed to the chamber 10 either directly from the operating circuit, or via a hydrocyclone 12 as illustrated. The hydrocyclone 12 serves to degrit the liquid to be tested. The overflow from the hydrocyclone is fed to the chamber 10 and the underflow is directed to waste through a pipe 9.

When the liquid encounters the sieve bend, larger particles entrained in the liquid are separated to waste, as shown by the arrow 14. In practice, coarse particles, greater than, say, 1 mm in diameter, have little effect on the accuracy of a viscosity reading, and the sieve is accordingly chosen to separate such particles.

Liquid passing the sieve bend enters the downwardly directed limb 15 of a U-shaped chamber 16. The flow parameters are chosen so that liquid continuously overflows a weir 17 at the head of the limb 15, so that there is always a substantially constant head of liquid in this limb. Liquid which overflows the weir 17 runs to waste through the pipe 13, as shown by the arrow 18.

The substantially constant head established by the weir 17 is at a higher elevation than the highest point in the other limb 19 of the chamber 16, so that the liquid flows continuously under gravity in a clockwise direction in the drawing. A drain pipe 20 is located at the lowest point of the chamber 16, so that liquid continuously runs to waste during operation of the apparatus.

The drain pipe reduces the flowrate of the liquid through the chamber 16 and also allows liquid in the apparatus to drain to waste in the event that the apparatus is non-operational for any period. In a case where the liquid under test is a ferrosilicon suspension or other suspension which could cause blockages in the apparatus at such times, as a result of solids settling, this is an important feature.

Liquid proceeding up the limb 19 of the chamber 16 enters an annular passage 21 surrounding a central passage 22. The flowrate of the liquid is chosen so that it overflows both into the passage 22 and into a launder 23 surrounding the outer wall of the annular passage 21. The outer wall of the passage 21 is formed with a series of apertures near its upper edge to allow overflow into the launder. The holes are slightly higher than the upper edge of the walls of the central passage 22, thus establishing a further check on the head of liquid delivered to the passage 22. Liquid overflowing to the launder 23 runs to waste through two diametrically opposed pipes 26. In other embodiments, there may be more than two such pipes 26.

The annular passage 21 is fitted with a series of equi-spaced, radially extending baffles 24 to promote laminar flow in the liquid. Likewise, the wall of the central passage 22 is fitted with radially extending baffles 25.

A bobbin 26 is suspended in the liquid overflowing into the passage 22 at the end of the output shaft of a constant speed D.C. motor 27. The motor serves to rotate the bobbin at constant angular velocity, and means 28 are used continuously to monitor the current drawn by the motor, and to provide a continuous hardcopy read-out of the viscosity of the liquid. The means 28 includes circuitry similar to that described in the specification of U.K. patent application no. 174377/77.

The liquid flowing past the bobbin runs to waste through a pipe 29. The pipe 29 is fitted with a throttle 30. The throttle 30, in the form of a restricted orifice plug connected at the lower end of the pipe, serves to adjust the flowrate characteristics through the apparatus to the desired level. Further adjustments to the flowrate can be effected by raising or lowering the level of the weir 17 at the head of the limb 15. This can be achieved by mounting the chamber 10 for limited up-and-down sliding movement in a fixed frame.

An important feature of the apparatus is the provision of a flushing spray ring 31 mounted co-axially above the passage 22. The ring is formed with a series of spaced holes on its underside, and is connected to a source of fresh water. The apparatus is fitted with a downwardly extending electrical probe 32. The probe extends to just below the level of the top of the walls of the passage 22. If the apparatus should cease to function for some reason, the liquid level drops below the probe and an electrical switching arrangement (not shown) acts to pass water through the spray ring 31. This serves to clean out the apparatus and prevent clogging of solids.

In practice, the apparatus is calibrated for a particular liquid suspension. A datum calibration can be obtained by testing a liquid of known viscosity, such as glycerine. The throttle 30 and the height of the weir 17 are then kept constant for the particular liquid which is to be tested.

Since it is essential that the motor speed be kept constant for accurate readings, it is provided with a resistance-heated jacket and a thermostatic control for ensuring a constant operating temperature.

Although this embodiment of the invention has been described with specific reference to the measurement of viscosity of a dense medium, such as a suspension, it should be appreciated that the principles of the invention are equally applicable to the measurement of the viscosity of liquids in general.

I claim:

1. An apparatus for the continuous measurement of the vicosity of a liquid flowing in a circuit, the apparatus, including means for continuously drawing off part of the flow of the liquid in the circuit, means for establishing a substantially constant static head in the liquid drawn off, means for allowing at least some of this liquid to flow at a constant flow rate under gravity past a rotor arranged to be rotated by a motor so that the liquid exerts a drag on the rotor in accordance with its viscosity and means for measuring an operating characteristic of the motor to give an indication of the viscosity of the liquid, and wherein the means for establishing a constant static head in the liquid drawn off includes a static head chamber provided with an overflow weir at a predetermined height above the rotor, the weir being situated at the head of a downwardly extending limb of a U-shaped chamber, the other limb of which extends upwardly to a level lower than that of the weir, so that liquid flowing under gravity through the chamber can overflow at the top of the other limb.

2. An apparatus according to claim 1, in which the height of the weir relative to the rotor is adjustable.

3. An apparatus according to claim 1, in which the upper end of the upwardly extending limb is arranged so that liquid flowing through the chamber overflows partially into a downwardly extending passage containing the rotor and partially to waste, with the overflow to waste being situated slightly higher than the overflow to the passage.

4. An apparatus according to claim 3, in which the upper end of the upwardly extending limb is arranged annularly about the downwardly extending passage containing the rotor.

5. An apparatus according to claim 3, including a throttle in the downwardly extending passage for controlling the flow rate of the liquid in the apparatus.

6. An apparatus according to claim 5, in which the throttle is in the form of a restricted orifice plug in the downwardly extending passage.

7. An apparatus according to claim 1, including a drain situated in the portion of the chamber linking the limbs to allow part of the liquid flowing through the chamber to flow to waste, and to allow liquid to escape from the chamber when the apparatus is not in use.

8. An apparatus according to claim 1, for use in measuring the viscosity of a dense suspension and including a cyclone for degritting the suspension drawn off from the circuit prior to the introduction of the cyclone overflow into the static head chamber.

9. An apparatus according to claim 8, including a sieve bend for separating out material in the suspension having a particle size greater than a predetermined size prior to the introduction of the suspension to the static head chamber, and a waste passage for directing the separated materials.

10. An apparatus according to claim 1, including flushing means arranged automatically to flush out the downwardly directed passage with water in the event of the apparatus ceasing to function.

11. An apparatus according to claim 10, in which the flushing means includes a flushing ring arranged to be supplied with water and to spray the water into the downwardly directed passage and a sensor arranged to detect when the upper level of liquid in the downwardly directed passage drops below a predetermined limit and to establish a flow of water to the flushing ring when such a drop is detected.

12. An apparatus according to claim 1, in which the motor is arranged to rotate the rotor at a constant angular speed, and the measuring means are arranged to make a continuous measurement of the current drawn by the motor.

13. An apparatus according to claim 12, in which the motor is a D.C. motor, and including means for keeping the motor temperature constant during operation.

14. An apparatus according to claim 13, in which the means for keeping the motor temperature constant includes a resistance-heated jacket with a thermostatic control.

15. An apparatus according to claim 1, in which the motor is arranged to be supplied with a constant current and in which the measuring means are arranged to measure the motor speed continuously.

* * * * *